(12) United States Patent
Prim

(10) Patent No.: US 8,505,332 B1
(45) Date of Patent: Aug. 13, 2013

(54) NATURAL GAS LIQUID RECOVERY PROCESS

(75) Inventor: Eric Prim, Midland, TX (US)

(73) Assignee: Pilot Energy Solutions, LLC, Houston, TX (US)

(*) Notice: Subject to any disclaimer, the term of this patent is extended or adjusted under 35 U.S.C. 154(b) by 1489 days.

(21) Appl. No.: 12/122,336

(22) Filed: May 16, 2008

Related U.S. Application Data

(60) Provisional application No. 60/938,726, filed on May 18, 2007.

(51) Int. Cl.
- F25J 3/00 (2006.01)
- C07C 7/00 (2006.01)
- C07C 7/10 (2006.01)
- C07C 7/144 (2006.01)

(52) U.S. Cl.
USPC .......... 62/618; 62/620; 62/928; 585/802; 585/818; 585/833

(58) Field of Classification Search
USPC .......... 62/617, 618, 620, 622; 585/818, 585/802, 833, 837
See application file for complete search history.

(56) References Cited

U.S. PATENT DOCUMENTS

| | | | |
|---|---|---|---|
| 4,136,738 A | 1/1979 | Haynes, Jr. et al. | |
| 4,374,657 A | 2/1983 | Schendel et al. | |
| 4,441,900 A | 4/1984 | Swallow | |
| 4,451,275 A | 5/1984 | Vines et al. | |
| 4,529,411 A * | 7/1985 | Goddin et al. | 95/51 |
| 4,563,202 A | 1/1986 | Yao et al. | |
| 4,595,404 A | 6/1986 | Ozero et al. | |
| 4,664,190 A | 5/1987 | Carpentier | |
| 4,683,948 A * | 8/1987 | Fleming | 166/402 |
| 4,762,543 A | 8/1988 | Pantermuehl et al. | |
| 4,765,407 A | 8/1988 | Yuvancic | |
| 5,019,279 A | 5/1991 | Haines et al. | |
| 5,411,721 A | 5/1995 | Doshi et al. | |
| 6,128,919 A * | 10/2000 | Daus et al. | 62/624 |
| 6,505,683 B2 | 1/2003 | Minkkinen et al. | |
| 6,648,944 B1 | 11/2003 | Baker et al. | |
| 6,915,662 B2 | 7/2005 | Wilkinson et al. | |
| 2003/0161780 A1* | 8/2003 | Howard et al. | 423/437.1 |
| 2008/0156035 A1* | 7/2008 | Aspelund et al. | 62/606 |
| 2011/0197629 A1* | 8/2011 | Prim et al. | 62/618 |

\* cited by examiner

*Primary Examiner* — Frantz Jules
*Assistant Examiner* — Keith Raymond
(74) *Attorney, Agent, or Firm* — Conley Rose, P.C.; Grant Rodolph; Nicholas K. Beaulieu

(57) ABSTRACT

A method comprising receiving a hydrocarbon feed stream, separating the hydrocarbon feed stream into a heavy hydrocarbon rich stream and a carbon dioxide recycle stream, separating the carbon dioxide recycle stream into a natural gas liquids (NGL) rich stream and a purified carbon dioxide recycle stream, and injecting the purified carbon dioxide recycle stream into a subterranean formation. Included is a method comprising selecting a first recovery rate for a NGL recovery process, estimating the economics of the NGL recovery process based on the first recovery rate, selecting a second recovery rate that is different from the first recovery rate, estimating the economics of the NGL recovery process based on the second recovery rate, and selecting the first recovery rate for the NGL recovery process when the estimate based on the first recovery rate is more desirable than the estimate based on the second recovery rate.

26 Claims, 4 Drawing Sheets

NATURAL GAS LIQUID RECOVERY PROCESS

CROSS-REFERENCE TO RELATED APPLICATIONS

The present application claims priority to U.S. Provisional Patent Application Ser. No. 60/938,726, filed May 18, 2007 by Eric Prim, and entitled "NGL Recovery Process," which is incorporated herein by reference as if reproduced in their entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Carbon dioxide ($CO_2$) is a naturally occurring substance in most hydrocarbon subterranean formations. Carbon dioxide may also be used for recovering or extracting oil and hydrocarbons from subterranean formations. One carbon dioxide based recovery process involves injecting carbon dioxide into an injection well, and recovering heavy hydrocarbons and perhaps some of the carbon dioxide from at least one recovery well. Carbon dioxide reinjection process may also produce natural gas liquids (NGLs).

SUMMARY

In one aspect, the disclosure includes a method comprising receiving a hydrocarbon feed stream, separating the hydrocarbon feed stream into a heavy hydrocarbon rich stream and a carbon dioxide recycle stream, separating the carbon dioxide recycle stream into a NGL rich stream and a purified carbon dioxide recycle stream, and injecting the purified carbon dioxide recycle stream into a subterranean formation.

In another aspect, the disclosure includes a plurality of process equipment configured to implement a method comprising receiving a recycle stream comprising at least one $C_{3+}$ hydrocarbon and a gas selected from the group consisting of carbon dioxide, nitrogen, air, and water, and separating the recycle stream into a NGL rich stream and a purified recycle stream, wherein the NGL rich stream comprises less than about 70 percent of the $C_{3+}$ hydrocarbons from the recycle stream.

In a third aspect, the disclosure includes a method comprising selecting a first recovery rate for a NGL recovery process, estimating the economics of the NGL recovery process based on the first recovery rate, selecting a second recovery rate that is different from the first recovery rate, estimating the economics of the NGL recovery process based on the second recovery rate, and selecting the first recovery rate for the NGL recovery process when the estimate based on the first recovery rate is more desirable than the estimate based on the second recovery rate.

DETAILED DESCRIPTION OF THE PREFERRED EMBODIMENTS

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

Disclosed herein is a NGL recovery process that may be implemented as part of a carbon dioxide reinjection process to recover NGLs from a carbon dioxide recycle stream. When implementing a carbon dioxide reinjection process, the carbon dioxide is typically injected downhole into an injection well and a stream comprising hydrocarbons and carbon dioxide is generally recovered from a recovery well. The carbon dioxide may be separated from the heavy hydrocarbons and then recycled downhole, e.g. in the reinjection well. In some cases, the carbon dioxide recycle stream may comprise some NGLs, which may be recovered prior to injecting the carbon dioxide recycle stream downhole. The NGL recovery process may be optimized by weighing the NGL recovery rate against the amount of energy expended on NGL recovery.

Figure 1:
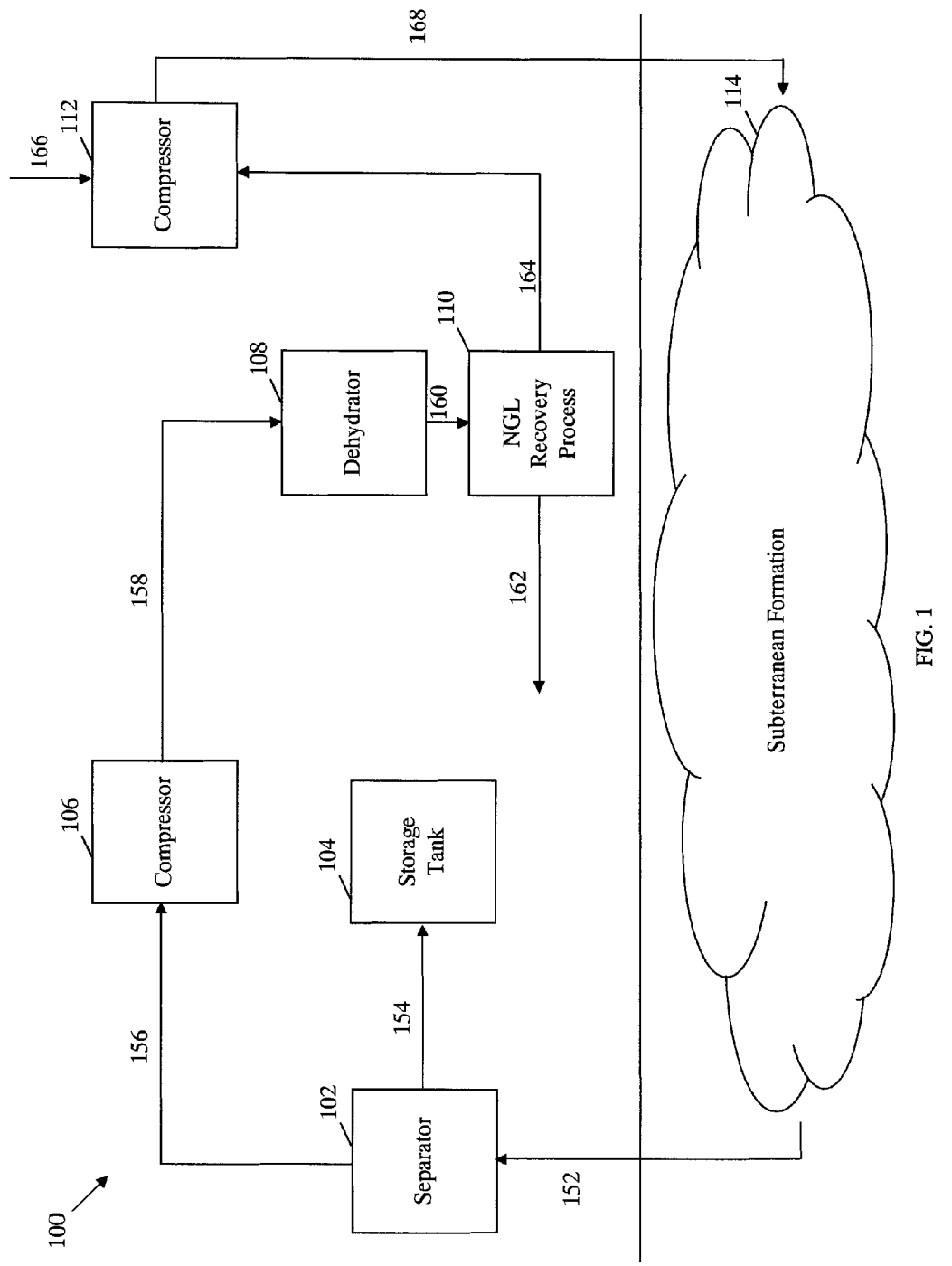
FIG. 1 is a process flow diagram for an embodiment of a carbon dioxide reinjection process.

FIG. 1 illustrates an embodiment of a carbon dioxide reinjection process 100. The carbon dioxide reinjection process 100 may receive hydrocarbons and carbon dioxide from a subterranean formation 114, separate heavy hydrocarbons and some of the NGLs from the carbon dioxide, and inject the carbon dioxide downhole. As shown in FIG. 1, additional process steps may be included in the carbon dioxide reinjection process, such as compressing the carbon dioxide, dehydrating the carbon dioxide, and/or adding additional carbon dioxide to the carbon dioxide recycle stream. The specific steps in the carbon dioxide reinjection process 100 are explained in further detail below.

The carbon dioxide reinjection process 100 may receive a hydrocarbon feed stream 152 from a subterranean formation 114. The hydrocarbon feed stream 152 may be obtained from at least one recovery well as indicated by the upward arrow in FIG. 1, but may also be obtained from other types of wells. In addition, the hydrocarbon feed stream 152 may be obtained from the subterranean formation 114 using any suitable method. For example, if a suitable pressure differential exists between the subterranean formation 114 and the surface, the hydrocarbon feed stream 152 may flow to the surface via the pressure differential. Alternatively, surface and/or downhole pumps may be used to draw the hydrocarbon feed stream 152 from the subterranean formation 114 to the surface.

Although the composition of the hydrocarbon feed stream 152 will vary from one location to another, the hydrocarbon feed stream 152 may comprise carbon dioxide, methane, ethane, NGLs, heavy hydrocarbons, hydrogen sulfide ($H_2S$), helium, nitrogen, water, or combinations thereof. The term "hydrocarbon" may refer to any compound comprising, consisting essentially of, or consisting of carbon and hydrogen atoms. The term "natural gas" may refer to any hydrocarbon that may exist in a gas phase under atmospheric or downhole conditions, and includes methane and ethane, but may also include diminishing amounts of $C_3$-$C_8$ hydrocarbons. The term "natural gas liquids" or NGLs may refer to natural gases that may be liquefied without refrigeration, and may include $C_3$-$C_8$ hydrocarbons. Both natural gas and NGL are terms known in the art and are used herein as such. In contrast, the term "heavy hydrocarbons" may refer to any hydrocarbon that may exist in a liquid phase under atmospheric or downhole conditions, and generally includes liquid crude oil, which may comprise $C_{9+}$ hydrocarbons, branched hydrocarbons, aromatic hydrocarbons, and combinations thereof.

The hydrocarbon feed stream 152 may enter a separator 102. The separator 102 may be any process equipment suitable for separating at least one inlet stream into a plurality of effluent streams having different compositions, states, temperatures, and/or pressures. For example, the separator 102 may be a column having trays, packing, or some other type of complex internal structure. Examples of such columns include scrubbers, strippers, absorbers, adsorbers, packed columns, and distillation columns having valve, sieve, or other types of trays. Such columns may employ weirs, downspouts, internal baffles, temperature control elements, and/or pressure control elements. Such columns may also employ some combination of reflux condensers and/or reboilers, including intermediate stage condensers and reboilers. Alternatively, the separator 102 may be a phase separator, which is a vessel that separates an inlet stream into a substantially vapor stream and a substantially liquid stream, such as a knock-out drum, flash drum, reboiler, condenser, or other heat exchanger. Such vessels may also have some internal baffles, temperature control elements, and/or pressure control elements, but generally lack any trays or other type of complex internal structure commonly found in columns. The separator 102 may also be any other type of separator, such as a membrane separator. In a specific embodiment, the separator 102 is a knockout drum. Finally, the separator 102 may be any combination of the aforementioned separators 102 arranged in series, in parallel, or combinations thereof.

The separator 102 may produce a heavy hydrocarbon stream 154 and a carbon dioxide recycle stream 156. The heavy hydrocarbon stream 154 may comprise most of the heavy hydrocarbons from the hydrocarbon feed stream 152. In embodiments, the heavy hydrocarbon stream 154 may comprise at least about 90 percent, at least about 95 percent, at least about 99 percent, or substantially all of the heavy hydrocarbons from the hydrocarbon feed stream 152. The heavy hydrocarbon stream 154 may be sent to a pipeline for transportation or a storage tank 104, where it is stored until transported to another location or further processed. In contrast, the carbon dioxide recycle stream 156 may comprise most of the carbon dioxide from the hydrocarbon feed stream 152. In embodiments, the carbon dioxide recycle stream 156 may comprise at least about 90 percent, at least about 95 percent, at least about 99 percent, or substantially all of the carbon dioxide from the hydrocarbon feed stream 152. Similarly, the carbon dioxide recycle stream 156 may comprise at least about 80 percent, at least about 90 percent, at least about 95 percent, or substantially all of the natural gas from the hydrocarbon feed stream 152. All of the percentages referred to herein are molar percentages until otherwise specified.

The carbon dioxide recycle stream 156 may enter a compressor 106. The compressor 106 may be any process equipment suitable for increasing the pressure, temperature, and/or density of an inlet stream. The compressor 106 may be configured to compress a substantially vapor phase inlet stream, a substantially liquid phase inlet stream, or combinations thereof. As such, the term "compressor" may include both compressors and pumps, which may be driven by electrical, mechanical, hydraulic, or pneumatic means. Specific examples of suitable compressors 106 include centrifugal, axial, positive displacement, turbine, rotary, and reciprocating compressors and pumps. In a specific embodiment, the compressor 106 is a turbine compressor. Finally, the compressor 106 may be any combination of the aforementioned compressors 106 arranged in series, in parallel, or combinations thereof.

The compressor 106 may produce a compressed carbon dioxide recycle stream 158. The compressed carbon dioxide recycle stream 158 may contain the same composition as the carbon dioxide recycle stream 156, but at a higher energy level. The additional energy in the compressed carbon dioxide recycle stream 158 may be obtained from energy added to the compressor 106, e.g. the electrical, mechanical, hydraulic, or pneumatic energy. In embodiments, difference in energy levels between the compressed carbon dioxide recycle stream 158 and the carbon dioxide recycle stream 156 is at least about 50 percent, at least about 65 percent, or at least about 80 percent of the energy added to the compressor 106.

The compressed carbon dioxide recycle stream 158 may enter a dehydrator 108. The dehydrator 108 may remove some or substantially all of the water from the compressed carbon dioxide recycle stream 158. The dehydrator 108 may be any suitable dehydrator, such as a condenser, an absorber, or an adsorber. Specific examples of suitable dehydrators 108 include refrigerators, molecular sieves, liquid desiccants such as glycol, solid desiccants such as silica gel or calcium chloride, and combinations thereof. The dehydrator 108 may also be any combination of the aforementioned dehydrators 108 arranged in series, in parallel, or combinations thereof. In a specific embodiment, the dehydrator 108 is a glycol unit. Any water accumulated within or exiting from the dehydrator 108 may be stored, used for other processes, or discarded.

The dehydrator 108 may produce a dehydrated carbon dioxide recycle stream 160. The dehydrated carbon dioxide recycle stream 160 may contain little water, e.g. liquid water or water vapor. In embodiments, the dehydrated carbon dioxide recycle stream 160 may comprise no more than about 5 percent, no more than about 3 percent, no more than about 1 percent, or be substantially free of water.

Figure 2:
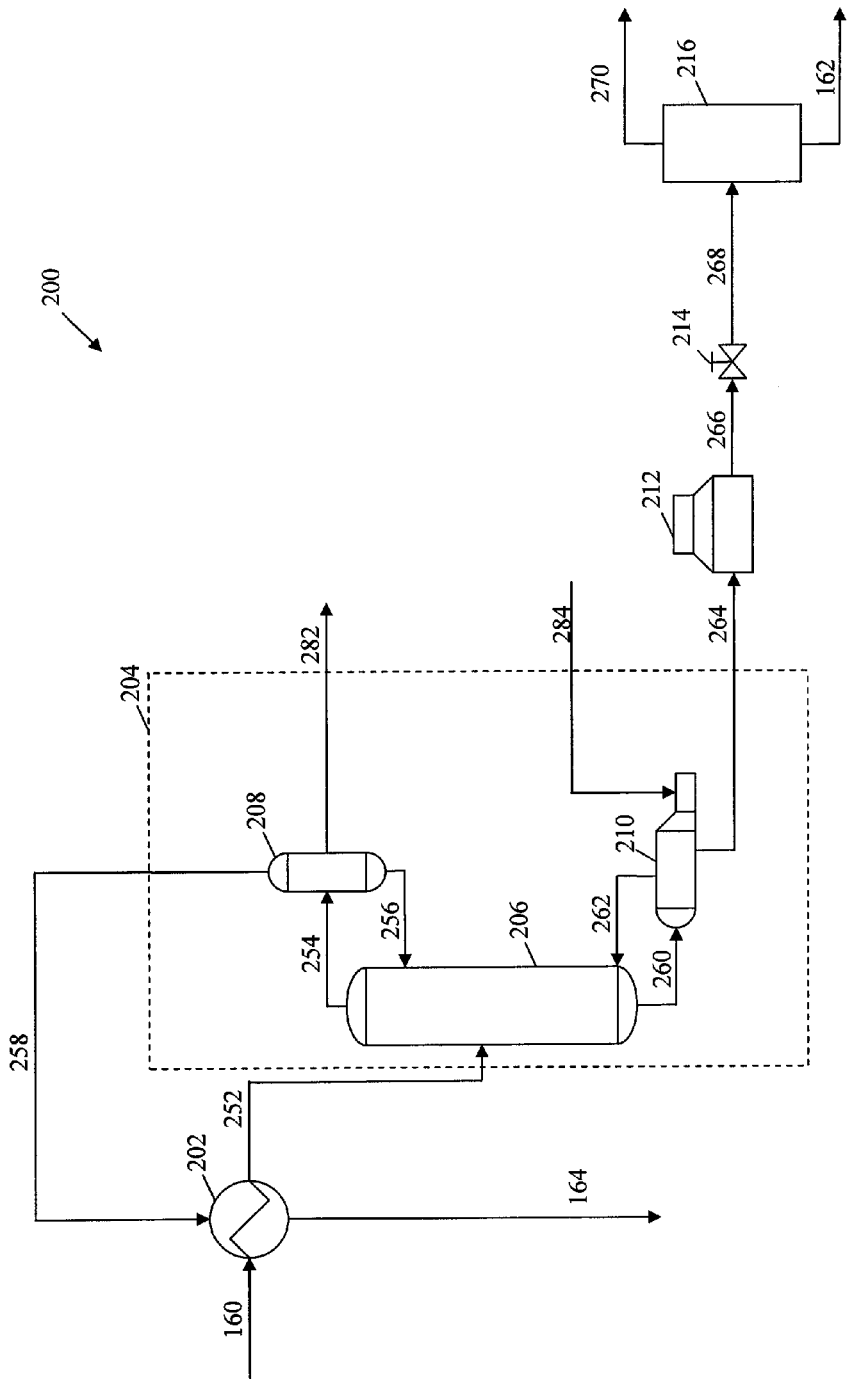
FIG. 2 is a schematic diagram of an embodiment of a NGL recovery process.

The dehydrated carbon dioxide recycle stream 160 may enter a NGL recovery process 110. The NGL recovery process 110 may separate the dehydrated carbon dioxide recycle stream 160 into a NGL rich stream 162 and a purified carbon dioxide recycle stream 164. The NGL rich stream 162 may only comprise a portion of the total NGLs from the dehydrated carbon dioxide recycle stream 160. For example, the NGL rich stream 162 may comprise less than about 70 percent, from about 10 percent to about 50 percent, or from about 20 percent to about 35 percent of the NGLs from the dehydrated carbon dioxide recycle stream 160. By taking a less aggressive cut of the NGLs and/or disregarding the recovery of methane, ethane, and optionally propane from the dehydrated carbon dioxide recycle stream 160, the NGL recovery process 110 may produce a relatively high quality NGL rich stream 162 with relatively little process equipment or energy. A specific example of a suitable NGL recovery process 110 is shown in FIG. 2 and described in further detail below.

As mentioned above, the NGL recovery process 110 may produce a relatively high-quality NGL rich stream 162. Specifically, while the NGL recovery process 110 recovers only a portion, e.g., about 20 to about 35 percent, of the NGLs in the dehydrated carbon dioxide recycle stream 160, the resulting NGL rich stream 162 is relatively lean with respect to methane, ethane, and acid gases. For example, the NGL rich stream 162 may comprise most of the butane and heavier components from the dehydrated carbon dioxide recycle stream 160. For example, the NGL rich stream 162 may comprise at least about 90 percent, at least about 95 percent, at least about 99 percent, or substantially all of the $C_{4+}$ from the dehydrated carbon dioxide recycle stream 160. In embodiments, the NGL rich stream 162 may comprise no more than about 10 percent, no more than about 5 percent, no more than about 1 percent, or be substantially free of ethane. Similarly, the NGL rich stream 162 may comprise no more than about 5 percent, no more than about 3 percent, no more than about 1 percent, or be substantially free of methane. Moreover, the NGL rich stream 162 may comprise no more than about 5 percent, no more than about 3 percent, no more than about 1 percent, or be substantially free of acid gases, such as carbon dioxide or hydrogen sulfide. It will be realized that the composition of the NGL rich stream 162 may be dependent on the dehydrated carbon dioxide recycle stream 160 composition. The examples provided below show the composition of the NGL rich stream 162 for three different dehydrated carbon dioxide recycle stream 160 compositions. The NGL rich stream 162 may be sent to a pipeline for transportation or a storage tank, where it is stored until transported to another location or further processed.

As mentioned above, the NGL recovery process 110 may produce a purified carbon dioxide recycle stream 164. The purified carbon dioxide recycle stream 164 may comprise most of the carbon dioxide from the dehydrated carbon dioxide recycle stream 160, as well as some other components such as methane, ethane, propane, butane, nitrogen, and hydrogen sulfide. In embodiments, the purified carbon dioxide recycle stream 164 may comprise at least about 90 percent, at least about 95 percent, at least about 99 percent, or substantially all of the carbon dioxide from the dehydrated carbon dioxide recycle stream 160. In addition, the purified carbon dioxide recycle stream 164 may comprise at least about 90 percent, at least about 95 percent, at least about 99 percent, or substantially all of the methane from the dehydrated carbon dioxide recycle stream 160. As such, the purified carbon dioxide recycle stream 164 may comprise at least about 65 percent, at least about 80 percent, at least about 90 percent, or at least about 95 percent carbon dioxide. In embodiments, the purified carbon dioxide recycle stream 164 may comprise no more than about 10 percent, no more than about 5 percent, no more than about 1 percent, or be substantially free of $C_{3+}$. Similarly, the purified carbon dioxide recycle stream 164 may comprise no more than about 20 percent, no more than about 10 percent, no more than about 5 percent, or be substantially free of $C_{2+}$.

The purified carbon dioxide recycle stream 164 may enter a compressor 112. The compressor 112 may comprise one or more compressors, such as the compressor 106 described above. In a specific embodiment, the compressor 112 is a turbine compressor. The compressor 112 may compress the purified carbon dioxide recycle stream 164, thereby producing a carbon dioxide injection stream 168. The carbon dioxide injection stream 168 may contain the same composition as the purified carbon dioxide recycle stream 164, but at a higher energy level. The additional energy in the carbon dioxide injection stream 168 may be obtained from energy added to the compressor 112, e.g. the electrical, mechanical, hydraulic, or pneumatic energy. In embodiments, difference in energy levels between the carbon dioxide injection stream 168 and the purified carbon dioxide recycle stream 164 is at least about 50 percent, at least about 65 percent, or at least about 80 percent of the energy added to the compressor 112.

In some embodiments, a makeup stream 166 may be combined with either the purified carbon dioxide recycle stream 164 or the carbon dioxide injection stream 168. Specifically, as the carbon dioxide reinjection process 100 is operated, carbon dioxide and other compounds will be lost, e.g. by replacing the hydrocarbons in the subterranean formation 114, by leakage into inaccessible parts of the subterranean formation 114, and/or to other causes. Alternatively, it may be desirable to increase the amount of carbon dioxide and other compounds injected downhole. As such, the makeup stream 166 may be combined with either the purified carbon dioxide recycle stream 164 and/or the carbon dioxide injection stream 168, for example in the compressor 112. Alternatively or additionally, the makeup stream 166 may be combined with the carbon dioxide recycle stream 156, the compressed carbon dioxide recycle stream 158, the dehydrated carbon dioxide recycle stream 160, or combinations thereof. The makeup stream 166 may comprise carbon dioxide, nitrogen, methane, ethane, air, water, or any other suitable compound. In an embodiment, the makeup stream 166 comprises at least 75 percent, at least 85 percent, or at least 95 percent carbon dioxide, nitrogen, methane, air, water, or combinations thereof.

FIG. 2 illustrates an embodiment of a NGL recovery process 200. The NGL recovery process 200 may recover some of the NGLs from a carbon dioxide recycle stream described above. For example, the NGL recovery process 200 may be implemented as part of the carbon dioxide reinjection process 100, e.g. by separating the dehydrated carbon dioxide recycle stream 160 into a NGL rich stream 162 and a purified carbon dioxide recycle stream 164.

The NGL recovery process 200 may begin by cooling the dehydrated carbon dioxide recycle stream 160 in a heat exchanger 202. The heat exchanger 202 may be any equipment suitable for heating or cooling one stream using another stream. Generally, the heat exchanger 202 is a relatively simple device that allows heat to be exchanged between two fluids without the fluids directly contacting each other. Examples of suitable heat exchangers 202 include shell and tube heat exchangers, double pipe heat exchangers, plate fin heat exchangers, bayonet heat exchangers, reboilers, condensers, evaporators, and air coolers. In the case of air coolers, one of the fluids is atmospheric air, which may be forced over tubes or coils using one or more fans. In a specific embodiment, the heat exchanger 202 is a shell and tube heat exchanger.

As shown in FIG. 2, the dehydrated carbon dioxide recycle stream 160 may be cooled using the cooled, purified carbon dioxide recycle stream 258. Specifically, the dehydrated carbon dioxide recycle stream 160 is cooled to produce the cooled carbon dioxide recycle stream 252, and the cooled, purified carbon dioxide recycle stream 258 is heated to produce the purified carbon dioxide recycle stream 164. The efficiency of the heat exchange process depends on several factors, including the heat exchanger design, the temperature, composition, and flowrate of the hot and cold streams, and/or the amount of thermal energy lost in the heat exchange process. In embodiments, the difference in energy levels between the dehydrated carbon dioxide recycle stream 160 and the cooled carbon dioxide recycle stream 252 is at least about 60 percent, at least about 70 percent, at least about 80, or at least about 90 percent of the difference in energy levels between the cooled, purified carbon dioxide recycle stream 258 and the purified carbon dioxide recycle stream 164.

The cooled carbon dioxide recycle stream 252 then enters a NGL stabilizer 204. The NGL stabilizer 204 may comprise a separator 206, a condenser 208, and a reboiler 210. The separator 206 may be similar to any of the separators described herein, such as separator 102. In a specific embodiment, the separator 206 is a distillation column. The condenser 208 may receive an overhead 254 from the separator 206 and produce the cooled, purified carbon dioxide recycle stream 258 and a reflux stream 256, which is returned to the separator 206. The condenser 208 may be similar to any of the heat exchangers described herein, such as heat exchanger 202. In a specific embodiment, the condenser 208 is a shell and tube, kettle type condenser coupled to a refrigeration process, and contains a reflux accumulator. As such, the condenser 208 may remove some energy 282 from the reflux stream 256 and cooled, purified carbon dioxide recycle stream 258, typically by refrigeration. The cooled, purified carbon dioxide recycle stream 258 is substantially similar in composition to the purified carbon dioxide recycle stream 164 described above. Similarly, the reboiler 210 may receive a bottoms stream 260 from the separator 206 and produce a sour NGL rich stream 264 and a boil-up stream 262, which is returned to the separator 206. The reboiler 210 may be like any of the heat exchangers described herein, such as heat exchanger 202. In a specific embodiment, the reboiler 210 is a shell and tube heat exchanger coupled to a hot oil heater. As such, the reboiler 210 adds some energy 284 to the boil-up stream 262 and the sour NGL rich stream 264, typically by heating. The sour NGL rich stream 264 may be substantially similar in composition to the NGL rich stream 162, with the exception that the sour NGL rich stream 264 has some additional acid gases, e.g. acid gases 270 described below.

The sour NGL rich stream 264 may then be cooled in another heat exchanger 212. The heat exchanger 212 may be like any of the heat exchangers described herein, such as heat exchanger 202. For example, the heat exchanger 212 may be an air cooler as described above. A cooled, sour NGL rich stream 266 exits the heat exchanger 212 and enters a throttling valve 214. The throttling valve 214 may be an actual valve such as a gate valve, globe valve, angle valve, ball valve, butterfly valve, needle valve, or any other suitable valve, or may be a restriction in the piping such as an orifice or a pipe coil, bend, or size reduction. The throttling valve 214 may reduce the pressure, temperature, or both of the cooled, sour NGL rich stream 266 and produce a low-pressure sour NGL rich stream 268. The cooled, sour NGL rich stream 266 and the low-pressure sour NGL rich stream 268 have substantially the same composition as the sour NGL rich stream 264, albeit with lower energy levels.

The low-pressure sour NGL rich stream 268 may then be sweetened in a separator 216. The separator 216 may be similar to any of the separators described herein, such as separator 102. In an embodiment, the separator 216 may be one or more packed columns that use a sweetening process to remove acid gases from the low-pressure sour NGL rich stream 268. Suitable sweetening processes include amine solutions, physical solvents such as SELEXOL or RECTISOL, mixed amine solution and physical solvents, potassium carbonate solutions, direct oxidation, absorption, adsorption using, e.g., molecular sieves, or membrane filtration. The separator 216 may produce the NGL rich stream 162 described above. In addition, any acid gases 270 accumulated within or exiting from the separator 216 may be stored, used for other processes, or suitably disposed of. Finally, while FIGS. 1 and 2 are described in the context of carbon dioxide reinjection, it will be appreciated that the concepts described herein can be applied to other reinjection processes, for example those using nitrogen, air, or water.

Figure 3:
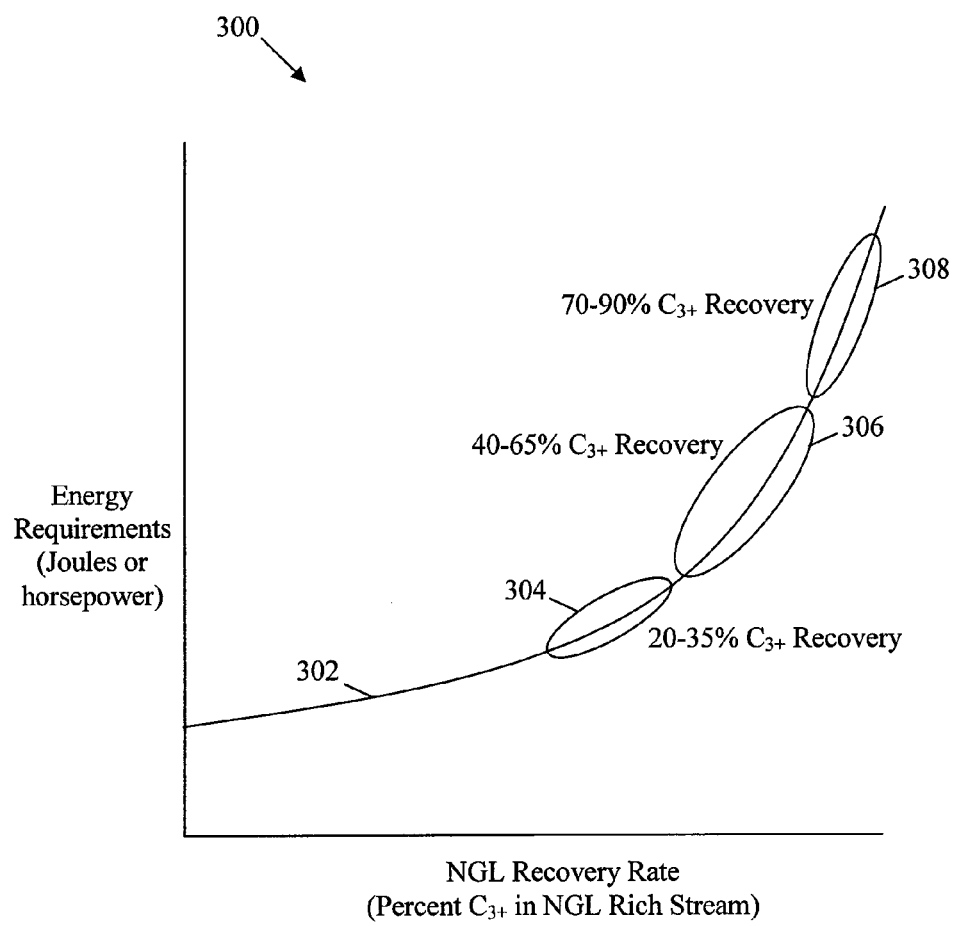
FIG. 3 is a chart depicting an embodiment of the relationship between the NGL recovery rate and the energy requirement.

FIG. 3 illustrates an embodiment of a chart 300 depicting the relationship between the NGL recovery rate and the energy expended to recover NGLs in the NGL recovery process. The NGL recovery rate may be a percentage recovery, and may represent the amount of $C_{3+}$ in the carbon dioxide recycle stream that is recovered in the NGL rich stream. The energy requirement may be measured in joules (J) or in horsepower (hp), and may represent the energy required to generate the condenser energy and reboiler energy described above. If additional compressors are needed at any point in the carbon dioxide reinjection process than would be required in an otherwise similar carbon dioxide reinjection process that lacks the NGL recovery process, then the energy required to operate such compressors may be included in the energy requirement shown in FIG. 3.

As shown by curve 302, the energy requirements may increase about exponentially as the NGLs are recovered at higher rates. In other words, substantially higher energy may be required to recover the NGLs at incrementally higher rates. For example, recovering a first amount 304 of from about 20 percent to about 35 percent of $C_{3+}$ may require substantially less energy than recovering a second amount 306 of from about 40 percent to about 65 percent of $C_{3+}$. Moreover, recovering the second amount 306 of from about 40 percent to about 65 percent of $C_{3+}$ may require substantially less energy than recovering a third amount 308 of from about 70 percent to about 90 percent of $C_{3+}$. Such significant reduction in energy requirements may be advantageous in terms of process feasibility and cost, where relatively small decreases in NGL recovery rates may require significantly less energy and process equipment, yielding significantly better process economics. Although the exact relationship of the curve 302 may depend on numerous factors especially the price of $C_{3+}$, in an embodiment the economics of the NGL recovery process when the NGL recovery rate is in the second amount 306 may be better than the economics of the NGL recovery process when the NGL recovery rate is in the third amount 308. Similarly, the economics of the NGL recovery process when the NGL recovery rate is in the first amount 304 may be significantly better than the economics of the NGL recovery process when the NGL recovery rate is in the second amount 306. Such a relationship is counterintuitive considering that in many other processes, the process economics generally improve with increased recovery rates.

Figure 4:
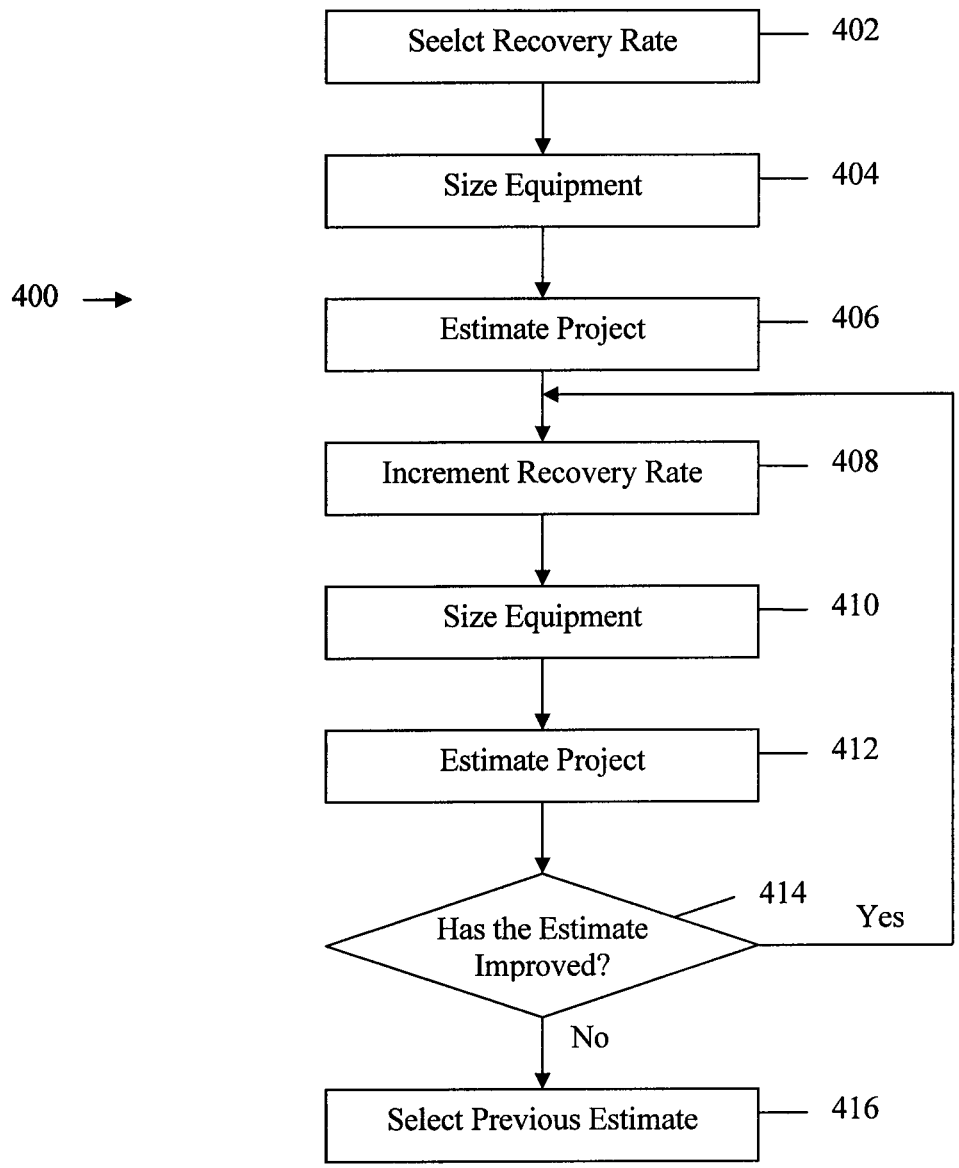
FIG. 4 is a flowchart of an embodiment of a NGL recovery optimization method.

FIG. 4 illustrates an embodiment of a NGL recovery optimization method 400. The NGL recovery optimization method 400 may be used to determine an improved or optimal project estimate for implementing the NGL recovery process and recovering NGLs at a suitable rate. As such, the NGL recovery process may be configured using appropriate equipment design based on the NGL recovery rate. Specifically, the NGL recovery optimization method 400 may design or configure the equipment size, quantity, or both based on an initial NGL recovery rate and required energy, and hence estimate the project feasibility and cost. The method 400 may upgrade or improve the project estimate by iteratively incrementing the initial NGL recovery rate, re-estimating the project, and comparing the two estimates.

At block 402, the method 400 may select an initial NGL recovery rate. The initial NGL recovery rate may be relatively small, such as no more than about 20 percent recovery, no more than about 10 percent recovery, no more than about 5 percent recovery, or no more than about 1 percent recovery. Choosing the initial NGL recovery rate at a small percentage of the total NGL amount may result in a relatively low project estimate that may be increased gradually to reach improved estimates.

The method 400 may then proceed to block 404, where the project equipment size may be determined based on the initial NGL recovery rate. Specifically, the size of the equipment described in the NGL recovery process and any additional compressors as described above may be determined. In addition, the pressure and temperature ratings and material compositions of such equipment may be determined at block 404, if desired.

The method 400 may then proceed to block 406, where the project may be estimated. Project estimation may comprise an economic evaluation of the NGL recovery process, and may include the cost of obtaining, fabricating, and/or field constructing the equipment sized in block 404. In addition, project estimation may include the cost of operating and maintaining the NGL process, as well as the revenue generated by the sale or use of the products obtained by implementing the NGL process. As such, the project estimate may comprise the total project benefits (including production, sales, etc.) minus the total project capital and operating costs (including cost, equipment, etc.). In some embodiments, the project estimate may be based on an existing carbon dioxide reinjection plant that lacks the NGL recovery process.

The method 400 may then proceed to block 408, where the recovery rate is incremented. The NGL recovery rate may be incremented by a relatively small percentage, for example no more than about 10 percent, not more than about 5 percent, or no more than about 1 percent. The method 400 may then proceed to block 410, which is substantially similar to block 404. The method 400 may then proceed to block 412, which is substantially similar to block 406.

The method 400 may then proceed to block 414, where the method 400 may determine whether the project estimate has improved. For instance, the method 400 may compare the project estimate from block 412 with the previous project estimate (either block 406 or the previous iteration of block 412) and determine whether the revised estimate is more economically desirable. The method 400 may return to block 408 when the condition at block 414 is met. Otherwise, the method 400 may proceed to block 416.

At block 416, the method 400 may choose the previous project estimate as the final estimate. For example, the method 400 may select the previous NGL recovery rate (either block 406 or the previous iteration of block 412) instead of the estimate obtained at block 412. In some embodiments, the desired or optimum recovery rate selected at block 416 may represent a range of desirable or optimum points, as opposed to a single point. Accordingly, the method 400 may select the equipment sizing corresponding to the selected NGL recovery rate. The selected project estimate and sizing may then be used for the NGL recovery process. Of course, it will be appreciated that the method 400 may be revised to include a decremented, top-down estimation approach as opposed to an incremented, bottom-up estimation approach.

The method 400 may have several advantages over other project estimation methods. For example, process equipment of a specific size may be selected, and the corresponding recovery rate determined. Alternatively, a required recovery rate may be selected, and the equipment sized to achieve the recovery rate. However, it has been discovered that such approaches are inflexible and often yields suboptimal process economics. For example, relatively high NGL recovery rates will not lead to an improvement in process economics, e.g. because of the exponential increase in energy consumption. In contrast, the method 400 provides a flexible approach to determining a desirable or optimal project estimate.

In an embodiment, the equipment size may be configured to allow for variations in recovery rates to accommodate changes in economic conditions, such as $C_{3+}$ or energy pricing. Specifically, the equipment described herein can be sized above or below the desired or optimum amount to allow the processes described herein to operate at recovery rates slightly greater than or slightly less than the desirable or optimum point obtained in method 400. As the process parameters and the energy requirements may be closely related, the ability of the process to continue to successfully operate under differing conditions may be reflected by constrained changes in the energy requirements of the process. When operating in the first amount 304 or the second amount 306 on the curve 302 in FIG. 3, significant increases or decreases in NGL recovery rate may be obtained with little change in the energy requirements. Such is not the case when operating in the third amount 308 on the curve 302 in FIG. 3, where significant increases or decreases in energy requirements yield only incremental changes in NGL recovery rate.

EXAMPLES

In one example, a process simulation was performed using the NGL recovery process 200 shown in FIG. 2. The simulation was performed using the Hyprotech Ltd. HYSYS Process v2.1.1 (Build 3198) software package. The NGL recovery process 200 separated the dehydrated carbon dioxide recycle stream 160 into the purified carbon dioxide recycle stream 164, the NGL rich stream 162, and the acid gas stream 270. The specified values are indicated by an asterisk (*). The physical properties are provided in degrees Fahrenheit (F), pounds per square inch gauge (psig), million standard cubic feet per day (MMSCFD), pounds per hour (lb/hr), U.S. gallons per minute (USGPM), and British thermal units per hour (Btu/hr). The material streams, their compositions, and the associated energy streams produced by the simulation are provided in tables 1, 2, and 3 below, respectively.

TABLE 1A

Material Streams

| Name | | Dehydrated $CO_2$ Recycle Stream 160 | Cooled $CO_2$ Recycle Stream 252 | Cooled, Purified $CO_2$ Recycle Stream 258 |
|---|---|---|---|---|
| Vapor Fraction | | 0.9838 | 0.9392 | 1.0000 |
| Temperature | (F.) | 104.0* | 45.00* | 4.011 |
| Pressure | (psig) | 340.0* | 335.0 | 330.0 |
| Molar Flow | (MMSCFD) | 17.00* | 17.00 | 15.88 |
| Mass Flow | (lb/hr) | 8.049e+04 | 8.049e+04 | 7.254e+04 |
| Liquid Volume Flow | (USGPM) | 218.1 | 218.1 | 192.3 |
| Heat Flow | (Btu/hr) | −2.639e+08 | −2.658e+08 | −2.577e+08 |

TABLE 1B

Material Streams

| Name | | Purified $CO_2$ Recycle Stream 164 | Sour NGL Rich Stream 264 | Cooled Sour NGL Rich Stream 266 |
|---|---|---|---|---|
| Vapor Fraction | | 1.0000 | 0.00000 | 0.0000 |
| Temperature | (F.) | 97.39 | 202.6 | 120.0* |
| Pressure | (psig) | 325.0 | 340.0 | 635.3* |
| Molar Flow | (MMSCFD) | 15.88 | 1.119 | 1.119 |

TABLE 1B-continued

Material Streams

| Name | | Purified $CO_2$ Recycle Stream 164 | Sour NGL Rich Stream 264 | Cooled Sour NGL Rich Stream 266 |
|---|---|---|---|---|
| Mass Flow | (lb/hr) | 7.254e+04 | 7947 | 7947 |
| Liquid Volume Flow | (USGPM) | 192.3 | 25.84 | 25.84 |
| Heat Flow | (Btu/hr) | −2.558e+08 | −8.443e+06 | −8.862e+06 |

TABLE 1C

Material Streams

| Name | | Low-Pressure Sour NGL Rich Stream 268 | Acid Gas Stream 270 | NGL Rich Stream 162 |
|---|---|---|---|---|
| Vapor Fraction | | 0.0000 | 1.0000 | 0.0000 |
| Temperature | (F.) | 120.9 | 100.0* | 111.8 |
| Pressure | (psig) | 200.3* | 5.304* | 185.3* |
| Molar Flow | (MMSCFD) | 1.119 | 0.1030 | 1.016 |
| Mass Flow | (lb/hr) | 7947 | 446.4 | 7501 |
| Liquid Volume Flow | (USGPM) | 25.84 | 1.100 | 24.74 |
| Heat Flow | (Btu/hr) | −8.862e+06 | −1.083e+06 | −7.779e+06 |

TABLE 2A

Stream Compositions

| Name | Dehydrated $CO_2$ Recycle Stream 160 | Cooled $CO_2$ Recycle Stream 252 | Cooled, Purified $CO_2$ Recycle Stream 258 |
|---|---|---|---|
| Comp Mole Frac ($H_2S$) | 0.0333* | 0.0333 | 0.0327 |
| Comp Mole Frac (Nitrogen) | 0.0054* | 0.0054 | 0.0058 |
| Comp Mole Frac ($CO_2$) | 0.7842* | 0.7842 | 0.8359 |
| Comp Mole Frac (Methane) | 0.0521* | 0.0521 | 0.0558 |
| Comp Mole Frac (Ethane) | 0.0343* | 0.0343 | 0.0348 |
| Comp Mole Frac (Propane) | 0.0406* | 0.0406 | 0.0313 |
| Comp Mole Frac (i-Butane) | 0.0072* | 0.0072 | 0.0022 |
| Comp Mole Frac (n-Butane) | 0.0171* | 0.0171 | 0.0015 |
| Comp Mole Frac (i-Pentane) | 0.0058* | 0.0058 | 0.0000 |
| Comp Mole Frac (n-Pentane) | 0.0057* | 0.0057 | 0.0000 |
| Comp Mole Frac (n-Hexane) | 0.0070* | 0.0070 | 0.0000 |
| Comp Mole Frac (n-Octane) | 0.0071* | 0.0071 | 0.0000 |
| Comp Mole Frac ($H_2O$) | 0.0000* | 0.0000 | 0.0000 |

TABLE 2B

Stream Compositions

| Name | Purified $CO_2$ Recycle Stream 164 | Sour NGL Rich Stream 264 | Cooled Sour NGL Rich Stream 266 |
|---|---|---|---|
| Comp Mole Frac ($H_2S$) | 0.0327 | 0.0421 | 0.0421 |
| Comp Mole Frac (Nitrogen) | 0.0058 | 0.0000 | 0.0000 |
| Comp Mole Frac ($CO_2$) | 0.8359 | 0.0500 | 0.0500 |
| Comp Mole Frac (Methane) | 0.0558 | 0.0000 | 0.0000 |
| Comp Mole Frac (Ethane) | 0.0348 | 0.0281 | 0.0281 |
| Comp Mole Frac (Propane) | 0.0313 | 0.1728 | 0.1728 |
| Comp Mole Frac (i-Butane) | 0.0022 | 0.0789 | 0.0789 |
| Comp Mole Frac (n-Butane) | 0.0015 | 0.2388 | 0.2388 |
| Comp Mole Frac (i-Pentane) | 0.0000 | 0.0887 | 0.0887 |
| Comp Mole Frac (n-Pentane) | 0.0000 | 0.0866 | 0.0866 |
| Comp Mole Frac (n-Hexane) | 0.0000 | 0.1063 | 0.1063 |

TABLE 2B-continued

Stream Compositions

| Name | Purified $CO_2$ Recycle Stream 164 | Sour NGL Rich Stream 264 | Cooled Sour NGL Rich Stream 266 |
|---|---|---|---|
| Comp Mole Frac (n-Octane) | 0.0000 | 0.1077 | 0.1077 |
| Comp Mole Frac ($H_2O$) | 0.0000 | 0.0000 | 0.0000 |

TABLE 2C

Stream Compositions

| Name | Low-Pressure Sour NGL Rich Stream 268 | Acid Gas Stream 270 | NGL Rich Stream 162 |
|---|---|---|---|
| Comp Mole Frac ($H_2S$) | 0.0421 | 0.4568 | 0.0000 |
| Comp Mole Frac (Nitrogen) | 0.0000 | 0.0000 | 0.0000 |
| Comp Mole Frac ($CO_2$) | 0.0500 | 0.5432 | 0.0000 |
| Comp Mole Frac (Methane) | 0.0000 | 0.0000 | 0.0000 |
| Comp Mole Frac (Ethane) | 0.0281 | 0.0000 | 0.0309 |
| Comp Mole Frac (Propane) | 0.1728 | 0.0000 | 0.1903 |
| Comp Mole Frac (i-Butane) | 0.0789 | 0.0000 | 0.0869 |
| Comp Mole Frac (n-Butane) | 0.2388 | 0.0000 | 0.2630 |
| Comp Mole Frac (i-Pentane) | 0.0887 | 0.0000 | 0.0977 |
| Comp Mole Frac (n-Pentane) | 0.0866 | 0.0000 | 0.0954 |
| Comp Mole Frac (n-Hexane) | 0.1063 | 0.0000 | 0.1171 |
| Comp Mole Frac (n-Octane) | 0.1077 | 0.0000 | 0.1186 |
| Comp Mole Frac ($H_2O$) | 0.0000 | 0.0000 | 0.0000 |

TABLE 3

Energy Streams

| Name | Heat Flow (Btu/hr) |
|---|---|
| Condenser Q Energy Stream 282 | 1.469e+06 |
| Reboiler Q Energy Stream 284 | 1.152e+06 |

In another example, the process simulation was repeated using a different dehydrated carbon dioxide recycle stream 160. The material streams, their compositions, and the associated energy streams produced by the simulation are provided in tables 4, 5, and 6 below, respectively.

TABLE 4A

Material Streams

| Name | Dehydrated $CO_2$ Recycle Stream 160 | Cooled $CO_2$ Recycle Stream 252 | Cooled, Purified $CO_2$ Recycle Stream 258 |
|---|---|---|---|
| Vapor Fraction | 0.9874 | 0.9286 | 1.0000 |
| Temperature (F) | 104.0* | 60.00* | 22.77 |
| Pressure (psig) | 685.3* | 680.3 | 590.0 |
| Molar Flow (MMSCFD) | 20.00* | 20.00 | 18.86 |
| Mass Flow (lb/hr) | 8.535e+04 | 8.535e+04 | 7.780e+04 |
| Liquid Volume Flow (USGPM) | 258.0 | 258.0 | 232.2 |
| Heat Flow (Btu/hr) | −2.741e+08 | −2.760e+08 | −2.683e+08 |

TABLE 4B

Material Streams

| Name | Purified CO$_2$ Recycle Stream 164 | Sour NGL Rich Stream 264 | Cooled Sour NGL Rich Stream 266 |
|---|---|---|---|
| Vapor Fraction | 1.0000 | 0.00000 | 0.0000 |
| Temperature (F) | 87.48 | 290.7 | 120.0* |
| Pressure (psig) | 585.0 | 600.0 | 635.3* |
| Molar Flow (MMSCFD) | 18.86 | 1.139 | 1.139 |
| Mass Flow (lb/hr) | 7.780e+04 | 7552 | 7552 |
| Liquid Volume Flow (USGPM) | 232.2 | 25.83 | 25.83 |
| Heat Flow (Btu/hr) | −2.663e+08 | −7.411e+06 | −8.371e+06 |

TABLE 4C

Material Streams

| Name | Low-Pressure Sour NGL Rich Stream 268 | Acid Gas Stream 270 | NGL Rich Stream 162 |
|---|---|---|---|
| Vapor Fraction | 0.0000 | 1.0000 | 0.0000 |
| Temperature (F) | 120.5 | 100.0* | 118.6 |
| Pressure (psig) | 200.3* | 5.304* | 185.3* |
| Molar Flow (MMSCFD) | 1.139 | 0.02943 | 1.110 |
| Mass Flow (lb/hr) | 7552 | 141.2 | 7411 |
| Liquid Volume Flow (USGPM) | 25.83 | 0.3421 | 25.49 |
| Heat Flow (Btu/hr) | −8.371e+06 | −5.301e+05 | −7.841e+06 |

TABLE 5A

Stream Compositions

| Name | Dehydrated CO$_2$ Recycle Stream 160 | Cooled CO$_2$ Recycle Stream 252 | Cooled, Purified CO$_2$ Recycle Stream 258 |
|---|---|---|---|
| Comp Mole Frac (H$_2$S) | 0.0004* | 0.0004 | 0.0004 |
| Comp Mole Frac (Nitrogen) | 0.0153* | 0.0153 | 0.0162 |
| Comp Mole Frac (CO$_2$) | 0.6592* | 0.6592 | 0.6975 |
| Comp Mole Frac (Methane) | 0.1813* | 0.1813 | 0.1922 |
| Comp Mole Frac (Ethane) | 0.0620* | 0.0620 | 0.0620 |
| Comp Mole Frac (Propane) | 0.0411* | 0.0411 | 0.0275 |
| Comp Mole Frac (i-Butane) | 0.0064* | 0.0064 | 0.0017 |
| Comp Mole Frac (n-Butane) | 0.0179* | 0.0179 | 0.0024 |
| Comp Mole Frac (i-Pentane) | 0.0040* | 0.0040 | 0.0000 |
| Comp Mole Frac (n-Pentane) | 0.0049* | 0.0049 | 0.0000 |
| Comp Mole Frac (n-Hexane) | 0.0030* | 0.0030 | 0.0000 |
| Comp Mole Frac (n-Octane) | 0.0045* | 0.0045 | 0.0000 |
| Comp Mole Frac (H$_2$O) | 0.0000* | 0.0000 | 0.0000 |

TABLE 5B

Stream Compositions

| Name | Purified CO$_2$ Recycle Stream 164 | Sour NGL Rich Stream 264 | Cooled Sour NGL Rich Stream 266 |
|---|---|---|---|
| Comp Mole Frac (H$_2$S) | 0.0004 | 0.0008 | 0.0008 |
| Comp Mole Frac (Nitrogen) | 0.0162 | 0.0000 | 0.0000 |
| Comp Mole Frac (CO$_2$) | 0.6975 | 0.0250 | 0.0250 |
| Comp Mole Frac (Methane) | 0.1922 | 0.0000 | 0.0000 |
| Comp Mole Frac (Ethane) | 0.0620 | 0.0613 | 0.0613 |
| Comp Mole Frac (Propane) | 0.0275 | 0.2670 | 0.2670 |
| Comp Mole Frac (i-Butane) | 0.0017 | 0.0836 | 0.0836 |
| Comp Mole Frac (n-Butane) | 0.0024 | 0.2751 | 0.2751 |
| Comp Mole Frac (i-Pentane) | 0.0000 | 0.0697 | 0.0697 |

TABLE 5B-continued

Stream Compositions

| Name | Purified CO$_2$ Recycle Stream 164 | Sour NGL Rich Stream 264 | Cooled Sour NGL Rich Stream 266 |
|---|---|---|---|
| Comp Mole Frac (n-Pentane) | 0.0000 | 0.0858 | 0.0858 |
| Comp Mole Frac (n-Hexane) | 0.0000 | 0.0527 | 0.0527 |
| Comp Mole Frac (n-Octane) | 0.0000 | 0.0790 | 0.0790 |
| Comp Mole Frac (H$_2$O) | 0.0000 | 0.0000 | 0.0000 |

TABLE 5C

Stream Compositions

| Name | Low-Pressure Sour NGL Rich Stream 268 | Acid Gas Stream 270 | NGL Rich Stream 162 |
|---|---|---|---|
| Comp Mole Frac (H$_2$S) | 0.0008 | 0.0315 | 0.0000 |
| Comp Mole Frac (Nitrogen) | 0.0000 | 0.0000 | 0.0000 |
| Comp Mole Frac (CO$_2$) | 0.0250 | 0.9685 | 0.0000 |
| Comp Mole Frac (Methane) | 0.0000 | 0.0000 | 0.0000 |
| Comp Mole Frac (Ethane) | 0.0613 | 0.0000 | 0.0629 |
| Comp Mole Frac (Propane) | 0.2670 | 0.0000 | 0.2740 |
| Comp Mole Frac (i-Butane) | 0.0836 | 0.0000 | 0.0858 |
| Comp Mole Frac (n-Butane) | 0.2751 | 0.0000 | 0.2824 |
| Comp Mole Frac (i-Pentane) | 0.0697 | 0.0000 | 0.0716 |
| Comp Mole Frac (n-Pentane) | 0.0858 | 0.0000 | 0.0881 |
| Comp Mole Frac (n-Hexane) | 0.0527 | 0.0000 | 0.0541 |
| Comp Mole Frac (n-Octane) | 0.0790 | 0.0000 | 0.0811 |
| Comp Mole Frac (H$_2$O) | 0.0000 | 0.0000 | 0.0000 |

TABLE 6

Energy Streams

| Name | Heat Flow (Btu/hr) |
|---|---|
| Condenser Q Energy Stream 282 | 1.884e+06 |
| Reboiler Q Energy Stream 284 | 2.211e+06 |

In a third example, the process simulation was repeated using a different dehydrated carbon dioxide recycle stream 160. The material streams, their compositions, and the associated energy streams produced by the simulation are provided in tables 7, 8, and 9 below, respectively.

TABLE 7A

Material Streams

| Name | Dehydrated $CO_2$ Recycle Stream 160 | Cooled $CO_2$ Recycle Stream 252 | Cooled, Purified $CO_2$ Recycle Stream 258 |
|---|---|---|---|
| Vapor Fraction | 1.0000 | 0.9988 | 1.0000 |
| Temperature (F) | 104.0* | 30.00* | 4.617 |
| Pressure (psig) | 340.0* | 335.0 | 330.0 |
| Molar Flow (MMSCFD) | 17.00* | 17.00 | 16.82 |
| Mass Flow (lb/hr) | 8.083e+04 | 8.083e+04 | 7.968e+04 |
| Liquid Volume Flow (USGPM) | 203.4 | 203.4 | 199.5 |
| Heat Flow (Btu/hr) | −3.016e+08 | −3.032e+08 | −3.025e+08 |

TABLE 7B

Material Streams

| Name | Purified $CO_2$ Recycle Stream 164 | Sour NGL Rich Stream 264 | Cooled Sour NGL Rich Stream 266 |
|---|---|---|---|
| Vapor Fraction | 1.0000 | 0.00000 | 0.0000 |
| Temperature (F) | 76.45 | 199.4 | 120.0* |
| Pressure (psig) | 325.0 | 340.0 | 635.3* |
| Molar Flow (MMSCFD) | 16.82 | 0.1763 | 0.1763 |
| Mass Flow (lb/hr) | 7.968e+04 | 1153 | 1153 |
| Liquid Volume Flow (USGPM) | 199.5 | 3.894 | 3.894 |
| Heat Flow (Btu/hr) | −3.009e+08 | −1.278e+06 | −1.340e+06 |

TABLE 7C

Material Streams

| Name | Low-Pressure Sour NGL Rich Stream 268 | Acid Gas Stream 270 | NGL Rich Stream 162 |
|---|---|---|---|
| Vapor Fraction | 0.0000 | 1.0000 | 0.0000 |
| Temperature (F) | 120.4 | 100.0* | 115.4 |
| Pressure (psig) | 200.3* | 5.304* | 185.3* |
| Molar Flow (MMSCFD) | 0.1763 | 0.01048 | 0.1659 |
| Mass Flow (lb/hr) | 1153 | 48.82 | 1105 |
| Liquid Volume Flow (USGPM) | 3.894 | 0.1188 | 3.776 |
| Heat Flow (Btu/hr) | −1.340e+06 | −1.653e+05 | −1.175e+06 |

TABLE 8A

Stream Compositions

| Name | Dehydrated $CO_2$ Recycle Stream 160 | Cooled $CO_2$ Recycle Stream 252 | Cooled, Purified $CO_2$ Recycle Stream 258 |
|---|---|---|---|
| Comp Mole Frac ($H_2S$) | 0.0031* | 0.0031 | 0.0030 |
| Comp Mole Frac (Nitrogen) | 0.0008* | 0.0008 | 0.0008 |
| Comp Mole Frac ($CO_2$) | 0.9400* | 0.9400 | 0.9493 |
| Comp Mole Frac (Methane) | 0.0219* | 0.0219 | 0.0222 |
| Comp Mole Frac (Ethane) | 0.0156* | 0.0156 | 0.0157 |
| Comp Mole Frac (Propane) | 0.0116* | 0.0116 | 0.0088 |
| Comp Mole Frac (i-Butane) | 0.0015* | 0.0015 | 0.0002 |
| Comp Mole Frac (n-Butane) | 0.0031* | 0.0031 | 0.0001 |
| Comp Mole Frac (i-Pentane) | 0.0007* | 0.0007 | 0.0000 |
| Comp Mole Frac (n-Pentane) | 0.0006* | 0.0006 | 0.0000 |
| Comp Mole Frac (n-Hexane) | 0.0005* | 0.0005 | 0.0000 |
| Comp Mole Frac (n-Octane) | 0.0006* | 0.0006 | 0.0000 |
| Comp Mole Frac ($H_2O$) | 0.0000* | 0.0000 | 0.0000 |

TABLE 8B

Stream Compositions

| Name | Purified $CO_2$ Recycle Stream 164 | Sour NGL Rich Stream 264 | Cooled Sour NGL Rich Stream 266 |
|---|---|---|---|
| Comp Mole Frac ($H_2S$) | 0.0030 | 0.0094 | 0.0094 |
| Comp Mole Frac (Nitrogen) | 0.0008 | 0.0000 | 0.0000 |
| Comp Mole Frac ($CO_2$) | 0.9493 | 0.0500 | 0.0500 |
| Comp Mole Frac (Methane) | 0.0222 | 0.0000 | 0.0000 |
| Comp Mole Frac (Ethane) | 0.0157 | 0.0000 | 0.0000 |
| Comp Mole Frac (Propane) | 0.0088 | 0.2794 | 0.2794 |
| Comp Mole Frac (i-Butane) | 0.0002 | 0.1265 | 0.1265 |
| Comp Mole Frac (n-Butane) | 0.0001 | 0.2985 | 0.2985 |
| Comp Mole Frac (i-Pentane) | 0.0000 | 0.0713 | 0.0713 |
| Comp Mole Frac (n-Pentane) | 0.0000 | 0.0617 | 0.0617 |
| Comp Mole Frac (n-Hexane) | 0.0000 | 0.0482 | 0.0482 |
| Comp Mole Frac (n-Octane) | 0.0000 | 0.0550 | 0.0550 |
| Comp Mole Frac ($H_2O$) | 0.0000 | 0.0000 | 0.0000 |

TABLE 8C

Stream Compositions

| Name | Low-Pressure Sour NGL Rich Stream 268 | Acid Gas Stream 270 | NGL Rich Stream 162 |
|---|---|---|---|
| Comp Mole Frac ($H_2S$) | 0.0094 | 0.1584 | 0.0000 |
| Comp Mole Frac (Nitrogen) | 0.0000 | 0.0000 | 0.0000 |
| Comp Mole Frac ($CO_2$) | 0.0500 | 0.8416 | 0.0000 |
| Comp Mole Frac (Methane) | 0.0000 | 0.0000 | 0.0000 |
| Comp Mole Frac (Ethane) | 0.0000 | 0.0000 | 0.0000 |
| Comp Mole Frac (Propane) | 0.2794 | 0.0000 | 0.2970 |
| Comp Mole Frac (i-Butane) | 0.1265 | 0.0000 | 0.1345 |
| Comp Mole Frac (n-Butane) | 0.2985 | 0.0000 | 0.3174 |
| Comp Mole Frac (i-Pentane) | 0.0713 | 0.0000 | 0.0758 |
| Comp Mole Frac (n-Pentane) | 0.0617 | 0.0000 | 0.0656 |
| Comp Mole Frac (n-Hexane) | 0.0482 | 0.0000 | 0.0512 |
| Comp Mole Frac (n-Octane) | 0.0550 | 0.0000 | 0.0584 |
| Comp Mole Frac ($H_2O$) | 0.0000 | 0.0000 | 0.0000 |

TABLE 9

| Energy Streams | |
|---|---|
| Name | Heat Flow (Btu/hr) |
| Condenser Q Energy Stream 282 | 6.236e+06 |
| Reboiler Q Energy Stream 284 | 5.666e+06 |

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Specifically, while the process is described in terms of a continuous process, it is contemplated that the process can be implemented as a batch process. In addition, where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc. Moreover, the percentages described herein may be mole fraction, weight fraction, or volumetric fraction.

Accordingly, the scope of protection is not limited by the description set out above but is only limited by the claims that follow, that scope including all equivalents of the subject matter of the claims. Each and every claim is incorporated into the specification as an embodiment of the present invention. Thus, the claims are a further description and are an addition to the preferred embodiments of the present invention. The discussion of a reference in the herein is not an admission that it is prior art to the present invention, especially any reference that may have a publication date after the priority date of this application. The disclosures of all patents, patent applications, and publications cited herein are hereby incorporated by reference, to the extent that they provide exemplary, procedural, or other details supplementary to those set forth herein.

What is claimed is:

1. A method comprising:
  receiving a hydrocarbon feed stream, wherein the hydrocarbon feed stream comprises carbon dioxide, natural gas liquid (NGL), heavy hydrocarbons, and acid gas, wherein the NGL comprises $C_3$-$C_8$ hydrocarbons, and wherein the heavy hydrocarbons comprise $C_{9+}$ hydrocarbons;
  separating the hydrocarbon feed stream into a heavy hydrocarbon rich stream and a carbon dioxide recycle stream, wherein the heavy hydrocarbon rich stream comprises the $C_{9+}$ hydrocarbons, and wherein the carbon dioxide recycle stream comprises the carbon dioxide, the $C_3$-$C_8$ hydrocarbons, and the acid gas;
  separating the carbon dioxide recycle stream into a sour NGL rich stream and a purified carbon dioxide recycle stream, wherein the sour NGL rich stream comprises the $C_3$-$C_8$ hydrocarbons and the acid gas, and wherein the purified carbon dioxide recycle stream comprises the carbon dioxide; and
  separating the sour NGL rich stream into a sweet NGL rich stream and an acid gas stream, wherein the sweet NGL rich stream comprises the $C_3$-$C_8$ hydrocarbons, and wherein the acid gas stream comprises the acid gas,
  wherein the carbon dioxide is not removed from the hydrocarbon feed stream and is not removed from the carbon dioxide recycle stream prior to separating the carbon dioxide recycle stream into the sour NGL rich stream and the purified carbon dioxide recycle stream, and
  wherein the hydrocarbon feed stream, the carbon dioxide recycle stream, and the sour NGL rich stream are not subjected to cryogenic conditions, membranes, and carbon dioxide recovery solvents between being received and being separated into the heavy hydrocarbon rich stream, the purified carbon dioxide recycle stream, the sweet NGL rich stream, and the acid gas stream.

2. The method of claim 1, further comprising:
  compressing the carbon dioxide recycle stream prior to separating the carbon dioxide recycle stream;
  dehydrating at least part of the carbon dioxide recycle stream using a dehydration solvent prior to separating the carbon dioxide recycle stream;
  combining a carbon dioxide makeup stream external to the method with the purified carbon dioxide recycle stream; and
  injecting the combined carbon dioxide makeup stream and the purified carbon dioxide recycle stream into a subterranean formation.

3. The method of claim 1, further comprising cooling the carbon dioxide recycle stream with the purified carbon dioxide recycle stream.

4. The method of claim 3, wherein the sweet NGL rich stream comprises no more than 1 molar percent methane, no more than 1 molar percent ethane, and no more than 1 molar percent acid gases.

5. The method of claim 1, wherein the sweet NGL rich stream comprises from 20 molar percent to 40 molar percent of the $C_{3+}$ hydrocarbons from the carbon dioxide recycle stream, and wherein the purified carbon dioxide recycle stream comprises at least 94 molar percent of the carbon dioxide, at least 94 molar percent of the methane, and at least 93 molar percent of the ethane from the carbon dioxide recycle stream.

6. The method of claim 1, wherein separating the carbon dioxide recycle stream into the sour NGL rich stream and the purified carbon dioxide recycle stream comprises:
  refluxing part of the purified carbon dioxide recycle stream;
  reboiling part of the sour NGL rich stream; and
  cooling and throttling the sour NGL rich stream.

7. The method of claim 6, wherein the sour NGL rich steam comprises no more than 5 molar percent carbon dioxide, no more than 1 molar percent methane, and no more than 5 molar percent ethane, and wherein the sweet NGL rich stream is substantially free of carbon dioxide.

8. The method of claim 1, further comprising:
  compressing the carbon dioxide recycle stream prior to separating the carbon dioxide recycle stream;
  dehydrating at least part of the carbon dioxide recycle stream using molecular sieves prior to separating the carbon dioxide recycle stream;
  combining a carbon dioxide makeup stream external to the method with the purified carbon dioxide recycle stream; and injecting the combined carbon dioxide makeup stream and the purified carbon dioxide recycle stream into a subterranean formation.

9. A method comprising:

receiving a hydrocarbon feed stream comprising at least one $C_{3+}$ hydrocarbon, at least one $C_{9+}$ hydrocarbon, acid gas, and a gas selected from the group consisting of carbon dioxide, nitrogen, air, and water;

separating the hydrocarbon feed stream into a heavy hydrocarbon rich stream and a recycle stream, wherein the heavy hydrocarbon rich stream comprises most of the $C_{9+}$ hydrocarbon in the hydrocarbon feed stream, wherein the recycle stream comprises most of the $C_{3+}$ hydrocarbon and most of the acid gas in the hydrocarbon feed stream, and wherein the acid gas is selected from the group consisting of carbon dioxide, nitrogen, air, and water;

separating the recycle stream into a sour natural gas liquid (NGL) rich stream and a purified recycle stream, wherein the sour NGL rich stream comprises some of the $C_{3+}$ hydrocarbon and some of the acid gas in the recycle stream, and wherein the purified recycle stream comprises most of the $C_{3+}$ hydrocarbon and most of the acid gas in the recycle stream; and separating the sour NGL rich stream into a sweet NGL rich stream and an acid gas stream, wherein the sweet NGL rich stream comprises substantially all of the $C_{3+}$ hydrocarbon in the sour NGL rich stream, and wherein the acid gas stream comprises substantially all of the acid gas in the sour NGL rich stream, wherein the hydrocarbon feed stream, the recycle stream, and the sour NGL rich stream are not subjected to cryogenic conditions, membranes, and carbon dioxide recovery solvents between being received and being separated into the heavy hydrocarbon rich stream, the sweet NGL rich stream, the purified recycle stream, and the acid gas stream, and wherein carbon dioxide, nitrogen, and air are not removed from the hydrocarbon feed stream and are not removed from the recycle stream prior to separating the recycle stream into the sour NGL rich stream and the purified recycle stream.

10. The method of claim 9, wherein the sweet NGL rich stream comprises at least 90 molar percent $C_{3+}$ hydrocarbons, wherein the sweet NGL rich stream comprises from 20 molar percent to 40 molar percent of the $C_{3+}$ hydrocarbons from the recycle stream, and wherein the purified recycle stream comprises at least 94 molar percent of the carbon dioxide, at least 94 molar percent of the methane, and at least 93 molar percent of the ethane from the recycle stream.

11. The method of claim 10, wherein the sweet NGL rich stream comprises no more than 5 molar percent ethane and no more than 1 molar percent methane, and wherein the purified recycle stream comprises no more than 10 molar percent $C_{2+}$.

12. The method of claim 9, wherein separating the recycle stream into the sour NGL rich stream and the purified recycle stream comprises:

refluxing part of the purified recycle stream;
reboiling part of the sour NGL rich stream; and
cooling and throttling the sour NGL rich stream.

13. The method of claim 12, further comprising:
cooling the sour NGL rich stream;
expanding the sour NGL rich stream; and
cooling the recycle stream using the purified recycle stream.

14. The method of claim 13, further comprising:
compressing the recycle stream prior to separating the recycle stream; and
dehydrating at least part of the recycle stream using a dehydration solvent after separating the hydrocarbon feed stream and prior to separating the recycle stream.

15. The method of claim 13, wherein the sour NGL rich steam comprises no more than 5 molar percent carbon dioxide, no more than 1 molar percent methane, and no more than 5 molar percent ethane, and wherein the sweet NGL rich stream is substantially free of carbon dioxide.

16. The method of claim 13, further comprising:
compressing the recycle stream prior to separating the recycle stream; and
dehydrating at least part of the recycle stream using molecular sieves after separating the hydrocarbon feed stream and prior to separating the recycle stream.

17. The method of claim 14, wherein the heavy hydrocarbon rich stream comprises at least 90 molar percent of the $C_{9+}$ hydrocarbons in the hydrocarbon feed stream, wherein the recycle stream comprises at least 90 molar percent of the carbon dioxide in the hydrocarbon feed stream, wherein the sweet NGL rich stream comprises at least 60 molar percent of the $C_{4+}$ hydrocarbons in the recycle stream, and wherein the purified recycle stream comprises at least 90 molar percent of the carbon dioxide and at least 90 molar percent of the methane in the recycle stream.

18. The method of claim 14, further comprising combining a carbon dioxide makeup stream from a source external to the method with the purified recycle stream and subsequently injecting the combined carbon dioxide makeup stream and the purified recycle stream into a subterranean formation.

19. A method comprising:

receiving a hydrocarbon feed stream, wherein the hydrocarbon feed stream comprises carbon dioxide, natural gas liquid (NGL), and heavy hydrocarbons, wherein the NGL comprises $C_3$-$C_8$ hydrocarbons, and wherein the heavy hydrocarbons comprise $C_{9+}$ hydrocarbons;

separating the hydrocarbon feed stream into a heavy hydrocarbon rich stream and a carbon dioxide recycle stream, wherein the heavy hydrocarbon rich stream comprises most of the $C_{9+}$ hydrocarbons in the hydrocarbon feed stream, and wherein the carbon dioxide recycle stream comprises most of the carbon dioxide and most of the $C_3$-$C_8$ hydrocarbons in the hydrocarbon feed stream;

separating the carbon dioxide recycle stream into a sour NGL rich stream and a purified carbon dioxide recycle stream, wherein the sour NGL rich stream comprises some of the $C_3$-$C_8$ hydrocarbons in the carbon dioxide recycle stream, and wherein the purified carbon dioxide recycle stream comprises most of the carbon dioxide in the carbon dioxide recycle stream;

separating the sour NGL rich stream into a sweet NGL rich stream and a carbon dioxide rich stream, wherein the sweet NGL rich stream comprises the substantially all of the $C_3$-$C_8$ hydrocarbons in the source NGL rich stream, and wherein the carbon dioxide rich stream comprises substantially all of the carbon dioxide in the sour NGL rich stream;

combining a carbon dioxide makeup stream from a source external to the method with the purified carbon dioxide recycle stream; and subsequently injecting the combined carbon dioxide makeup stream and the purified carbon dioxide recycle stream into a subterranean formation, wherein the carbon dioxide is not removed from the hydrocarbon feed stream and is not removed from the carbon dioxide recycle stream prior to separating the carbon dioxide recycle stream into the sour NGL rich stream and the purified carbon dioxide recycle stream, and wherein the hydrocarbon feed stream, the carbon dioxide recycle stream, and the sour NGL rich stream are not subjected to cryogenic conditions, membranes, and carbon dioxide recovery solvents between being received and being separated into the heavy hydrocarbon rich stream, the purified carbon dioxide recycle stream, the sweet NGL rich stream, and the carbon dioxide rich stream.

20. The method of claim 19, further comprising:

compressing the carbon dioxide recycle stream prior to separating the carbon dioxide recycle stream;

dehydrating at least part of the carbon dioxide recycle stream using a dehydration solvent after separating the hydrocarbon feed stream and prior to separating the carbon dioxide recycle stream; and cooling the carbon dioxide recycle stream with the purified carbon dioxide recycle stream.

21. The method of claim 20, further comprising:

cooling the sour NGL rich stream;

expanding the sour NGL rich stream; and cooling the carbon dioxide recycle stream using the purified carbon dioxide recycle stream.

22. The method of claim 19, wherein the heavy hydrocarbon rich stream comprises at least 90 molar percent of the $C_{9+}$ hydrocarbons in the hydrocarbon feed stream, wherein the carbon dioxide recycle stream comprises at least 90 molar percent of the carbon dioxide in the hydrocarbon feed stream, wherein the sweet NGL rich stream comprises at least 60 molar percent of the $C_{4+}$ hydrocarbons in the carbon dioxide recycle stream, wherein the sweet NGL rich stream comprises no more than 5 molar percent ethane and no more than 1 molar percent methane, wherein the purified carbon dioxide recycle stream comprises at least 90 molar percent of the carbon dioxide and at least 90 molar percent of the methane from the carbon dioxide recycle stream, and wherein the purified carbon dioxide recycle stream comprises no more than 10 molar percent $C_{2+}$.

23. The method of claim 19, wherein separating the carbon dioxide recycle stream into the sour NGL rich stream and the purified carbon dioxide recycle stream comprises:

refluxing part of the purified carbon dioxide recycle stream;

reboiling part of the sour NGL rich stream; and cooling and throttling the sour NGL rich stream.

24. The method of claim 23, wherein the sour NGL rich steam comprises no more than 5 molar percent carbon dioxide, no more than 1 molar percent methane, and no more than 5 molar percent ethane, and wherein the sweet NGL rich stream is substantially free of carbon dioxide.

25. The method of claim 19, wherein the sweet NGL rich stream comprises at least 90 molar percent $C_{3+}$ hydrocarbons, wherein the sweet NGL rich stream comprises from 20 molar percent to 40 molar percent of the $C_{3+}$ hydrocarbons from the recycle stream, and wherein the purified carbon dioxide recycle stream comprises at least 94 molar percent of the carbon dioxide, at least 94 molar percent of the methane, and at least 93 molar percent of the ethane from the carbon dioxide recycle stream.

26. The method of claim 19, further comprising:

compressing the carbon dioxide recycle stream prior to separating the carbon dioxide recycle stream;

dehydrating at least part of the carbon dioxide recycle stream using molecular sieves after separating the hydrocarbon feed stream and prior to separating the carbon dioxide recycle stream; and cooling the carbon dioxide recycle stream with the purified carbon dioxide recycle stream.

\* \* \* \* \*